United States Patent
Oexman et al.

(10) Patent No.: US 8,768,520 B2
(45) Date of Patent: Jul. 1, 2014

(54) SYSTEMS AND METHODS FOR CONTROLLING A BEDROOM ENVIRONMENT AND FOR PROVIDING SLEEP DATA

(75) Inventors: Robert D. Oexman, Carthage, MO (US); David B. Scott, Carthage, MO (US)

(73) Assignee: Kingsdown, Inc., Mebane, NC (US)

( * ) Notice: Subject to any disclaimer, the term of this patent is extended or adjusted under 35 U.S.C. 154(b) by 87 days.

(21) Appl. No.: 12/919,189

(22) PCT Filed: Nov. 14, 2008

(86) PCT No.: PCT/US2008/083608
§ 371 (c)(1), (2), (4) Date: Aug. 24, 2010

(87) PCT Pub. No.: WO2009/108228
PCT Pub. Date: Sep. 3, 2009

(65) Prior Publication Data
US 2011/0010014 A1  Jan. 13, 2011

Related U.S. Application Data

(60) Provisional application No. 61/031,235, filed on Feb. 25, 2008.

(51) Int. Cl.
*G06F 19/00* (2011.01)

(52) U.S. Cl.
USPC .................................. 700/276; 5/421; 5/600

(58) Field of Classification Search
CPC ... A61G 7/057; A61G 7/05769; A61G 7/002; A47C 31/21; A47C 27/14; Y10S 5/935
USPC ............ 700/276, 277, 278; 600/26, 300, 549, 600/595; 236/44; 607/107, 104; 5/423, 421, 5/593, 713, 600
See application file for complete search history.

(56) References Cited

U.S. PATENT DOCUMENTS 3,462,778 A   8/1969   Whitney
3,786,676 A   1/1974   Korolyshun et al.
(Continued)

FOREIGN PATENT DOCUMENTS

GB   2373189 A   9/2002
JP   2000-189472 A   7/2000
(Continued)

OTHER PUBLICATIONS

Diffrient, Niels et al., Humanscale 1/2/3, 1974, The MIT Press, Cambridge.

(Continued)

*Primary Examiner* — Kidest Bahta
(74) *Attorney, Agent, or Firm* — Sughrue Mion, PLLC

(57) ABSTRACT

A system for controlling a bedroom environment includes an environmental data collector configured to collect environmental data relating to the bedroom environment; a sleep data collector configured to collect sleep data relating to a person's state of sleep; an analysis unit configured to analyze the collected environmental data and the collected sleep data and to determine an adjustment of the bedroom environment that promotes sleep of the person; and a controller configured to effect the adjustment of the bedroom environment. A method for controlling a bedroom environment includes collecting environmental data relating to the bedroom environment; collecting sleep data relating to a person's state of sleep; analyzing the collected environmental data and the collected sleep data; determining an adjustment to the bedroom environment that promotes sleep; and communicating the adjustment to a device that effects the bedroom environment.

44 Claims, 7 Drawing Sheets

(56) References Cited

U.S. PATENT DOCUMENTS

| | | | |
|---|---|---|---|
| 4,466,385 A * | 8/1984 | Waryasz | 122/510 |
| 4,501,034 A | 2/1985 | Greenawalt | |
| 4,656,334 A * | 4/1987 | Endo et al. | 219/212 |
| 4,982,466 A | 1/1991 | Higgins et al. | |
| 5,020,176 A * | 6/1991 | Dotson | 5/710 |
| 5,062,169 A | 11/1991 | Kennedy et al. | |
| 5,105,488 A | 4/1992 | Hutchinson et al. | |
| 5,148,706 A | 9/1992 | Masuda et al. | |
| 5,231,717 A | 8/1993 | Scott et al. | |
| 5,283,735 A | 2/1994 | Gross et al. | |
| 5,299,428 A * | 4/1994 | Kawaguri et al. | 62/176.6 |
| 5,446,933 A * | 9/1995 | Gabelhouse | 5/670 |
| 5,625,914 A * | 5/1997 | Schwab | 5/690 |
| 5,636,396 A | 6/1997 | Workman et al. | |
| 5,848,450 A | 12/1998 | Oexman et al. | |
| 5,850,644 A * | 12/1998 | Hsia | 5/422 |
| 5,948,303 A * | 9/1999 | Larson | 219/486 |
| 5,963,997 A * | 10/1999 | Hagopian | 5/654 |
| 5,987,675 A | 11/1999 | Kim | |
| 5,989,258 A * | 11/1999 | Hattori | 606/80 |
| 6,008,598 A * | 12/1999 | Luff et al. | 318/16 |
| 6,212,718 B1 | 4/2001 | Stolpmann et al. | |
| 6,220,088 B1 | 4/2001 | Scales et al. | |
| 6,226,792 B1 * | 5/2001 | Goiffon et al. | 717/120 |
| 6,269,505 B1 | 8/2001 | Wilkinson | |
| 6,327,725 B1 | 12/2001 | Veilleux et al. | |
| 6,384,715 B1 * | 5/2002 | Potter | 340/407.1 |
| 6,421,858 B1 * | 7/2002 | Cuerel | 5/713 |
| 6,468,234 B1 | 10/2002 | Van der Loos et al. | |
| 6,560,803 B2 | 5/2003 | Zur | |
| 6,571,192 B1 | 5/2003 | Hinshaw et al. | |
| 6,585,328 B1 | 7/2003 | Oexman et al. | |
| 6,662,393 B2 | 12/2003 | Boyd | |
| 6,687,935 B2 | 2/2004 | Reeder et al. | |
| 6,741,950 B2 | 5/2004 | Hinshaw et al. | |
| 6,878,121 B2 | 4/2005 | Krausman et al. | |
| 6,916,236 B2 * | 7/2005 | Terpstra | 451/358 |
| 6,986,182 B2 | 1/2006 | Mossbeck | |
| 6,990,425 B2 | 1/2006 | Hinshaw et al. | |
| 7,036,172 B2 * | 5/2006 | Torbet et al. | 5/727 |
| 7,041,049 B1 | 5/2006 | Raniere | |
| 7,127,759 B2 | 10/2006 | Koops | |
| 7,685,658 B2 | 3/2010 | Lokhorst et al. | |
| 7,725,967 B2 | 6/2010 | Simmerer et al. | |
| 7,764,180 B2 * | 7/2010 | Huang | 340/573.1 |
| 7,802,618 B2 * | 9/2010 | Simon et al. | 165/254 |
| RE41,809 E | 10/2010 | Hinshaw et al. | |
| 7,877,827 B2 * | 2/2011 | Marquette et al. | 5/423 |
| 8,122,546 B2 * | 2/2012 | Chambers et al. | 5/722 |
| 2003/0125899 A1 | 7/2003 | Hinshaw et al. | |
| 2003/0208848 A1 | 11/2003 | Flick et al. | |
| 2004/0139549 A1 | 7/2004 | Mohrekesh et al. | |
| 2004/0177449 A1 | 9/2004 | Wong et al. | |
| 2004/0215416 A1 | 10/2004 | Hinshaw et al. | |
| 2005/0121530 A1 * | 6/2005 | Song | 236/44 C |
| 2005/0143617 A1 | 6/2005 | Auphan | |
| 2005/0166326 A1 | 8/2005 | Chaffee | |
| 2006/0112489 A1 | 6/2006 | Bobey et al. | |
| 2006/0143831 A1 | 7/2006 | Wu | |
| 2006/0179573 A1 | 8/2006 | Nissen et al. | |
| 2006/0236460 A1 | 10/2006 | Hooper | |
| 2007/0021965 A1 | 1/2007 | Boyd | |
| 2007/0056112 A1 | 3/2007 | Graebe | |
| 2007/0061974 A1 | 3/2007 | Gabbay | |
| 2007/0061976 A1 | 3/2007 | Bazargani | |
| 2007/0086947 A1 | 4/2007 | Boyd | |
| 2007/0118026 A1 | 5/2007 | Kameyama et al. | |
| 2007/0199154 A1 | 8/2007 | Escaross | |
| 2007/0227594 A1 | 10/2007 | Chaffee | |
| 2007/0238935 A1 | 10/2007 | Boyd | |
| 2008/0244831 A1 | 10/2008 | Kenmochi | |
| 2008/0307582 A1 | 12/2008 | Flocard et al. | |
| 2009/0006027 A1 | 1/2009 | Hinshaw | |
| 2009/0240514 A1 | 9/2009 | Oexman et al. | |
| 2010/0313359 A1 | 12/2010 | Scott et al. | |
| 2010/0317930 A1 | 12/2010 | Oexman et al. | |
| 2010/0318239 A1 | 12/2010 | Oexman et al. | |
| 2011/0010249 A1 | 1/2011 | Oexman et al. | |
| 2011/0163885 A1 | 7/2011 | Poulos et al. | |

FOREIGN PATENT DOCUMENTS

| | | |
|---|---|---|
| WO | 9732509 A1 | 9/1997 |
| WO | 9963314 A1 | 12/1999 |
| WO | 00/51470 A1 | 9/2000 |
| WO | 2005104904 A1 | 11/2005 |
| WO | 2006023479 A2 | 3/2006 |
| WO | 2007/053150 A1 | 5/2007 |

OTHER PUBLICATIONS

Diffrient, Niels et al., Humanscale 4/5/6, 1981, The MIT Press, Cambridge.

Tilley, Alvin R., The Measure of Man and Woman, 2002, John Wiley & Sons, New York.

Jacobson, Bert H. et al., "Subjective Rating of Perceived Back Pain, Stiffness and Sleep Quality Following Introduction of Medium-Firm Bedding Systems," Journal of Chiropractic Medicine, Winter 2006, pp. 128-134, vol. 5, No. 4, National University of Health Sciences.

Dement, William C., "History of Sleep Physiology and Medicine," in Principles and Practice of Sleep Medicine, eds. Meir H. Kryger, Thomas Roth, and William C. Dement, 4th Edition, 2005, Elsevier Inc., Philadelphia.

Raymann et al., "Skin Deep: Enhanced Sleep Depth by Cutaneous Temperature Manipulation," Brain: A Journal of Neurology, 2008, pp. 500-513, vol. 131, Oxford University Press.

European Search Report dated Sep. 9, 2011 for EP08872440.6.

European Search Report dated Sep. 12, 2011 for EP08872303.6.

Russian Office Action dated Jun. 8, 2011 for RU 2010135586.

Singapore Patent Office Action dated Feb. 27, 2012 for SG 201005897-2.

Iber, Conrad et al., The AASM Manual for the Scoring of Sleep and Associated Events: Rules, Terminology and Technical Specifications, 1st ed., 2007, American Academy of Sleep Medicine, Westchester, Illinois.

Office Action issued Oct. 1, 2013, in U.S. Appl. No. 13/712,351.

Office Action issued Oct. 1, 2013, in U.S. Appl. No. 13/712,213.

International Search Report and Written Opinion dated Apr. 10, 2012, for PCT/US2011/050122.

Chinese Office Action dated Dec. 4, 2013 for Chinese application 200880128584.3.

Office Action dated Feb. 25, 2014, issued in U.S. Appl. No. 13/712,351.

Office Action dated Mar. 6, 2014, issued in U.S. Appl. No. 13/712,213.

* cited by examiner

SYSTEMS AND METHODS FOR CONTROLLING A BEDROOM ENVIRONMENT AND FOR PROVIDING SLEEP DATA

CROSS-REFERENCE TO RELATED PATENT APPLICATION

This application claims priority from U.S. Provisional Patent Application No. 61/031,235, filed on Feb. 25, 2008, in the U.S. Patent and Trademark Office, the disclosure of which is incorporated herein by reference in its entirety.

BACKGROUND

1. Technical Field

Systems and methods consistent with the present invention relate to controlling a bedroom environment and to providing data to a person relating to their sleep experience. In particular, these systems and methods relate to measuring, analyzing and controlling environmental aspects of a bedroom and a sleep system to promote a healthy sleep period.

2. Description of the Related Art

As described in "History of Sleep Physiology and Medicine," by William C. Dement, for example, there has been scientific interest in sleep for many years. However, despite sleep-related discoveries such as the electrical activity of the brain, the arousal systems, the circadian system, and rapid eye movement sleep, the field of sleep medicine as a medical field has emerged only recently (i.e., within the last forty years). The field of sleep medicine is rapidly evolving as new sleep problems are recognized, new treatments are delivered, new sleep related needs are recognized, and an understanding of the complexity of sleep is developed.

A wide variety of factors influence a person's quality of sleep. Among these factors, the environmental aspects of a bedroom and a sleep system, are especially important. For example, environmental factors including, but not limited to, ambient temperature, near-body temperature, relative humidity, near-body humidity, ambient lighting, sound, etc., can all affect a person's quality of sleep either independently or in combination. As discussed herein, a sleep system may comprise all aspects of a bedding assembly including, but not limited to, mattresses, box springs, foundation units, bed frames, pillows, mattress pads, linens and, more generally, to any type of sleep product that influences a person's sleep.

Conventional devices can detect whether a person is snoring and thereafter adjust a mattress to an inclined position in response to such detections. Such conventional systems employ load cell technology, according to which one or possibly two force sensors are placed underneath a mattress to measure weight changes over the sensors. Conventional systems have also been developed to remotely control room lighting and room temperature, however such control is based on the personal preferences of a user and performed by the user consciously and intentionally. Further, conventional systems have been developed that employ heating or cooling elements for a mattress.

However, there is a need for systems and methods that continuously measure and analyze how a person is sleeping and, based on such measurements, automatically control many different environmental aspects of the person's bedroom and sleep system so as to continuously provide the person with the most suitable bedroom and sleep system environment throughout the night and, thereby, promote better sleep. There is also a need for such systems that are integrated into a mattress, rather than having sensors disposed separately underneath the mattress. Moreover, there is a need for systems and methods that automatically control the environmental aspects of the person's bedroom and sleep system based on how a person is sleeping, rather than, or in addition to, the person's personal preferences and the person's conscious control of those environmental aspects.

SUMMARY

Systems and methods for controlling a bedroom environment are described herein that measure environmental aspects of a bedroom and sleep system using sensing devices in the bedroom and/or in the sleep system and/or on the person. The information from the sensing devices is collected by a controller and analyzed. Correlations between environmental aspects and quality of sleep can be determined. The controller then communicates adjustments to be made to the various systems controlling the bedroom environment including, but not limited to, the heating, ventilating, and air conditioning ("HVAC") system, sleep system, humidifier/dehumidifier unit, lighting system, sound system, etc., so as to promote a healthy sleep period for the person.

An aspect of the present invention provides a system for controlling a bedroom environment, the system comprising: an environmental data collector configured to collect environmental data relating to the bedroom environment; a sleep data collector configured to collect sleep data relating to a person's state of sleep; an analysis unit configured to analyze the collected environmental data and the collected sleep data and to determine an adjustment of the bedroom environment that promotes sleep of the person; and a controller configured to effect the adjustment of the bedroom environment.

Another aspect of the present invention provides a method for controlling a bedroom environment, the method comprising: collecting environmental data relating to the bedroom environment; collecting sleep data relating to a person's state of sleep; analyzing the collected environmental data and the collected sleep data; determining an adjustment to the bedroom environment that promotes sleep; and communicating the adjustment to a device that effects the bedroom environment.

Another aspect of the present invention provides a computer readable storage medium comprising instructions for causing a computer to execute a method comprising: collecting environmental data relating to the bedroom environment; collecting sleep data relating to a person's state of sleep; analyzing the collected environmental data and the collected sleep data; determining an adjustment to the bedroom environment that promotes sleep; and communicating the adjustment to a device that effects the bedroom environment.

Another aspect of the present invention provides a system for providing sleep data, the system comprising: an environmental data collector configured to collect environmental data relating to a bedroom environment; a sleep data collector configured to collect sleep data relating to the person's state of sleep; an analysis unit configured to analyze the collected environmental data and the collected sleep data and to correlate changes in the person's state of sleep with the collected environmental data; and a data providing unit configured to provide data relating to said correlation.

BRIEF DESCRIPTION OF THE DRAWINGS

The above and other aspects of the present invention will become more apparent by describing in detail illustrative embodiments thereof with reference to the attached drawings, in which.

DETAILED DESCRIPTION OF ILLUSTRATIVE EMBODIMENTS

Figure 1:
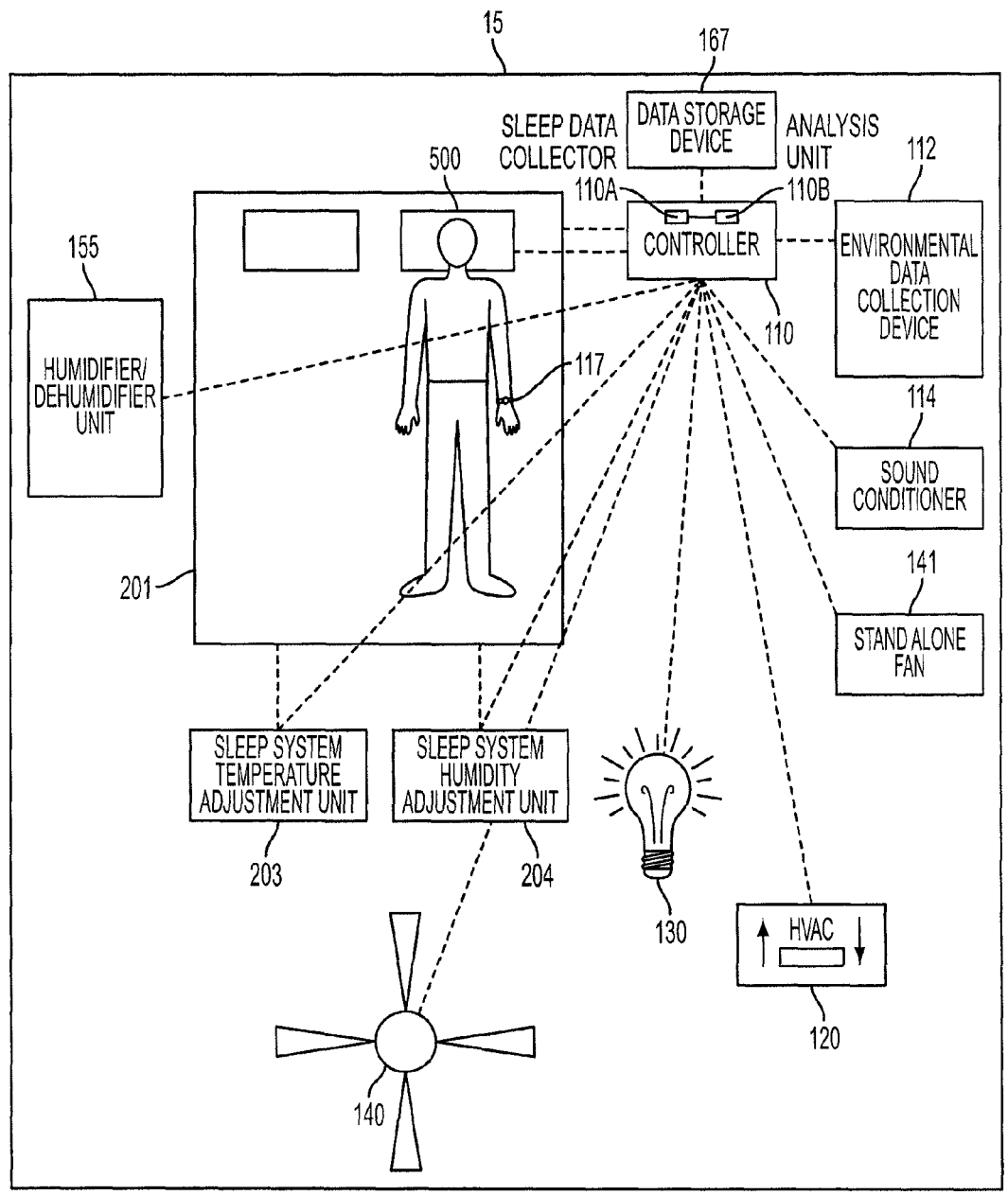
FIG. 1 illustrates a schematic view of a system for controlling a bedroom environment according to an illustrative embodiment of the present invention.

Hereinafter, illustrative embodiments of the present invention will be described in detail with reference to the attached drawings. FIG. 1 illustrates a schematic view of a system for controlling a bedroom environment according to an embodiment of the present invention. As shown in FIG. 1, a bedroom 15 comprises a sleep system 201, such as a bed, which is connected to a controller 110. The controller 110 comprises a sleep data collector 110A, which collects data related to sleep of person(s) disposed on the sleep system 201, and an analysis unit 110B. The sleep system 201, in turn, is connected to a sleep system temperature adjustment unit 203 and a sleep system humidity adjustment unit 204.

According to an embodiment, the sleep system temperature adjustment unit 203 may include a wide variety of conventional heating and cooling mechanisms. For example, the sleep system temperature adjustment unit 203 may comprise a heating pad configured to heat a surface of the sleep system 201 and/or an area surrounding the sleep system 201. Additionally, the sleep system temperature adjustment unit 203 may comprise a cooling fan, an electric heating pad, or a fluid cooling mechanism integrated into the sleep system 201, configured to cool the area surrounding the sleep system 201. Likewise, the sleep system humidity adjustment unit 204 may comprise a wide variety of conventional humidity control mechanisms that are configured to increase or decrease the relative humidity of the area surrounding the sleep system 201. Such heating, cooling and humidity adjustments can be controlled, for example, using conventional control units such as the LogicData's FLEX-5M-5.7.4.KD or the Morphy Richards FUD01 Climate Control Mattress Topper.

As shown in FIG. 1, the controller 110 is connected to a heating, ventilating, and air conditioning ("HVAC") system 120, a lighting system 130, a ceiling fan 140, a standalone fan 141, a humidifier/dehumidifier unit 155 and a sound conditioner 114. The sound conditioner 14 may comprise, for example, a device comparable to the Marsona 1288A Programmable Sound Conditioner, but the present invention is not limited to this example. The controller 110 is also connected to an environmental data collection device 112 and a data storage device 167. Consistent with the present invention, the aforementioned connections may comprise any of a wide variety of wireless and/or wired connections. Further, the present invention is not limited to the illustrative configuration shown in FIG. 1 and the controller 110 may be connected to any device that can affect the environment in which the person sleeps.

According to the embodiment shown in FIG. 1, the sleep system 201 comprises a variable sleep system like that disclosed by the inventors of the present application in a related provisional application U.S. Provisional No. 61/028,591 entitled, "Apparatuses and Methods Providing Variable Support and Variable Comfort Control of a Sleep System and Automatic Adjustment Thereof," which is incorporated herein by reference in its entirety. However, the present invention is not limited to such a variable sleep system and a wide variety of sleep systems can be employed consistent with the present invention.

Figure 2:
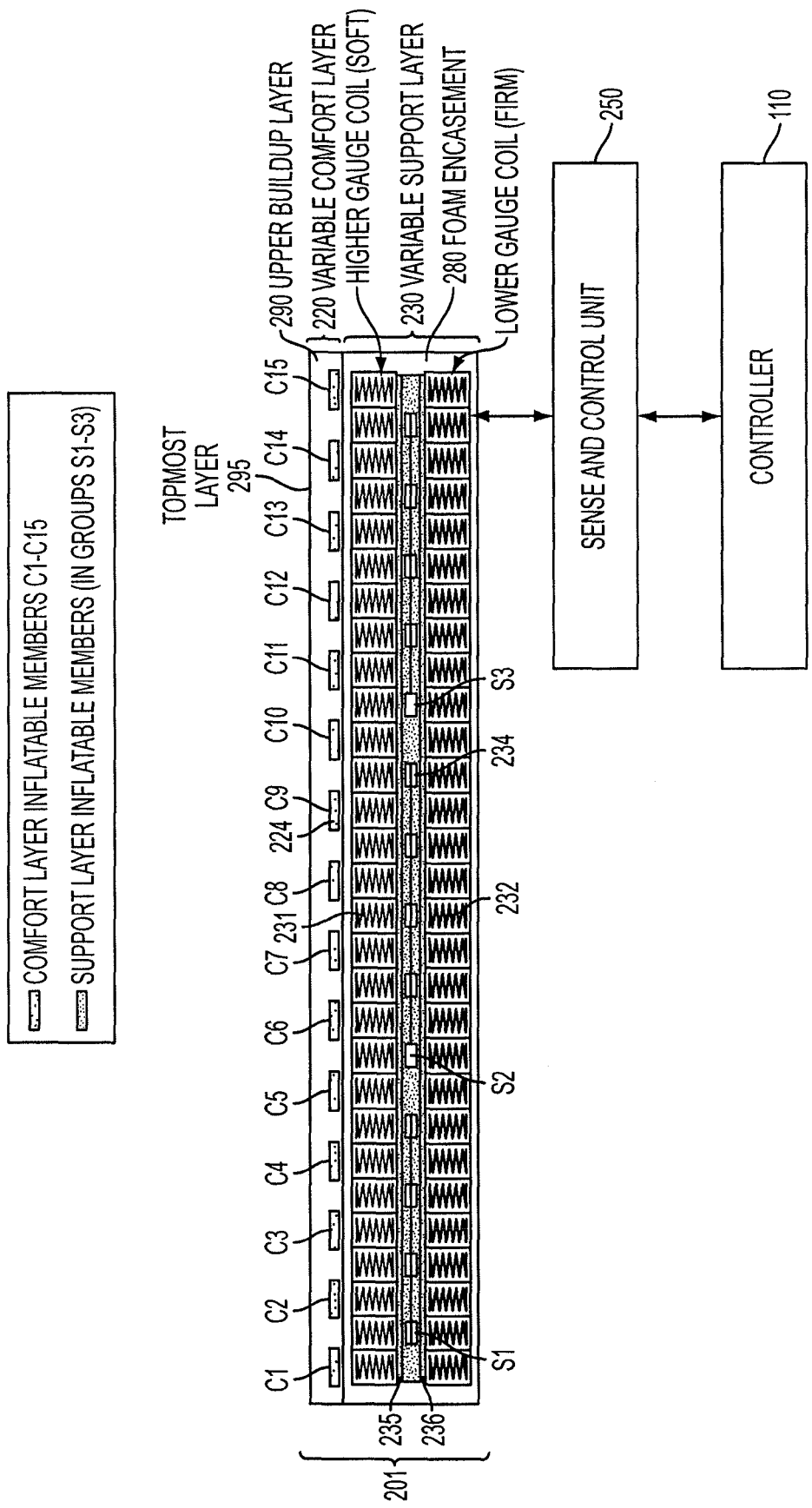
FIG. 2 illustrates a cross-sectional view of a variable sleep system employing a variable support and comfort control system according to an illustrative embodiment of the present invention.

FIG. 2 illustrates a cross-sectional view of sleep system 201 employing a variable support and comfort control system according to an embodiment of the present invention. As shown in FIG. 2, a variable support and variable comfort sleep system 201 comprises a variable comfort layer 220 and a variable support layer 230 that is disposed below the variable comfort layer 220. The variable comfort layer 220 further comprises an upper buildup layer 290 and a topmost layer 295. Further, as shown in FIG. 2, the variable sleep system 201 is connected to a sense and control unit 250.

By adjusting both the variable comfort layer 220 and the variable support layer 230, it is possible to adjust the variable sleep system 201 so that it provides the best possible combination of zoned comfort and support to the person. Adjustments to the variable comfort layer 220 and the variable support layer 230 may be performed automatically based on body variances of the person, or manually based on the person's comfort and support preferences.

FIG. 2 shows an embodiment wherein the variable support layer 230 comprises a layer of upper coils 231 and a layer of lower coils 232. As shown in FIG. 2, the layer of upper coils 231 and the layer of lower coils 232 are enclosed by a foam encasement 280. A plurality of support layer inflatable members or bladders 234 are disposed between the layer of upper coils 231 and the layer of lower coils 232. As shown in FIG. 2, there are three groups of support layer inflatable members 234, which are respectively referenced as S1, S2 and S3. However, the present invention is not limited to the configuration shown in FIG. 2 and any number of groups of support layer inflatable members 234 may be employed. According to the embodiment shown in FIG. 2, the support layer inflatable members 234 are pneumatic and are connected to an optional pump/vacuum unit (shown in FIG. 3) via pneumatic tubes. However, the present invention is not limited to this illustrative configuration and other gasses or fluids may be employed to inflate/deflate the support layer inflatable members 234 to a desired pressure.

The support layer inflatable members 234 may be constructed of a variety of materials including, but not limited to plastic, vinyl, neoprene, rubber and the like. According to the embodiment shown in FIG. 2, the support layer inflatable members 234 extend in a lateral direction across the width of the variable sleep system 201. According to an illustrative embodiment, for a sleep system designed to accommodate two people, such as a queen or king size bed, two sets of support layer inflatable members are employed, each extending across the area in which one of the people would sleep.

As shown in FIG. 2, the support layer inflatable members 234 are configured such that, when inflated, the support layer inflatable members 234 apply forces to the layer of upper coils 231 and to the layer of lower coils 232. Accordingly, by controlling the inflation/deflation of the support layer inflatable members 234, the support characteristics of the variable sleep system 201 can be adjusted.

Figure 3:
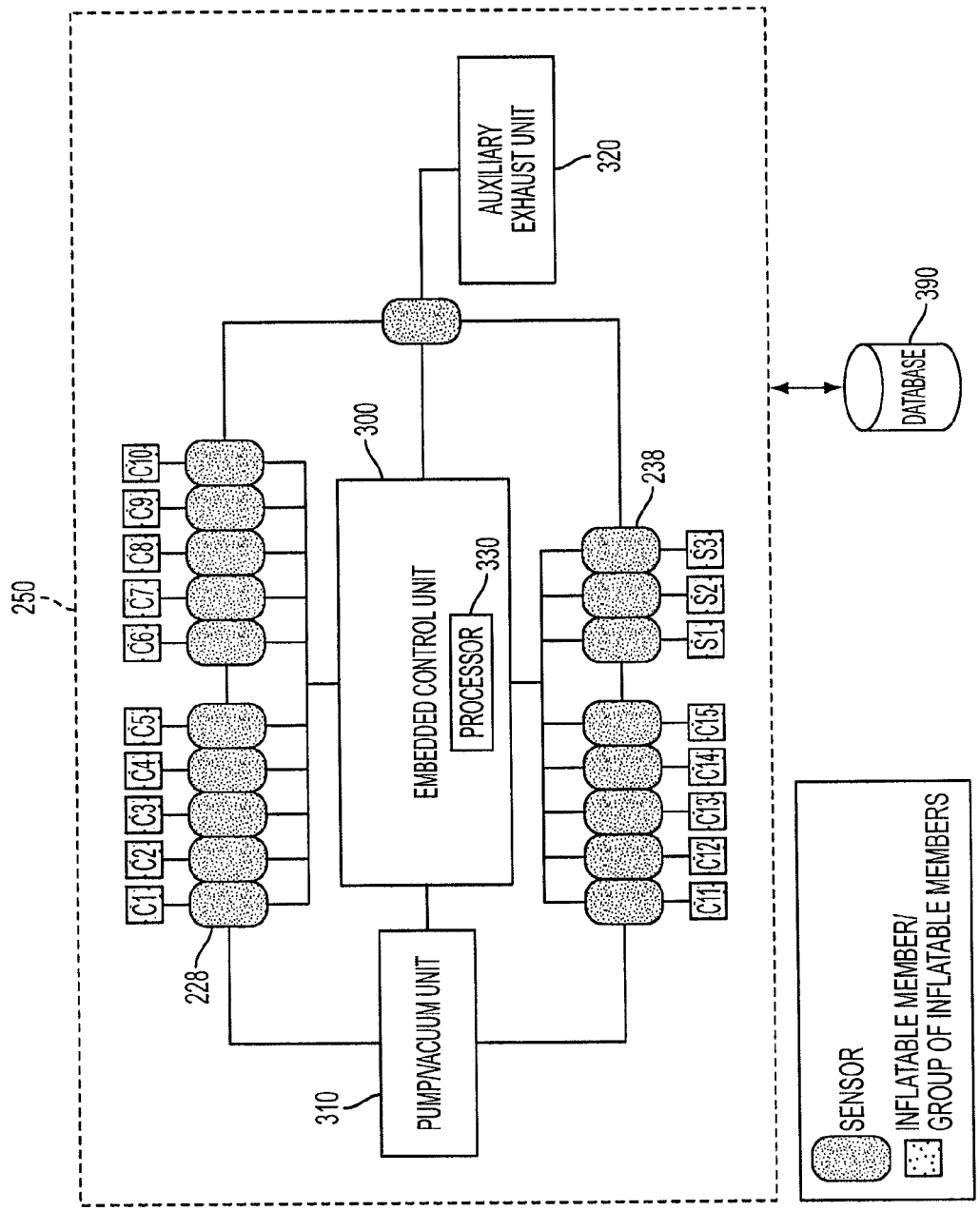
FIG. 3 illustrates a sense and control unit according to an illustrative embodiment of the present invention.

As shown in FIG. 2, the variable sleep system 201 is connected to a sense and control unit 250, which is in turn connected to the controller 110. A detailed illustration of an illustrative sense and control unit 250 is shown in FIG. 3. As shown in FIG. 3, the sense and control unit 250 comprises a plurality of comfort layer sensors 228, which are respectively associated with the comfort layer inflatable members 224, which are respectively referenced as C1, C2, C3, C4, C5, C6, C7, C8, C9, C10, C11, C12, C13, C14 and C15. The sense and control unit 250 further comprises a plurality of support layer sensors 238, which are respectively associated with the groups S1, S2 and S3 of support layer inflatable members 234. As further illustrated in FIG. 3, the sense and control unit 250 comprises an embedded control unit 300, a pump/vacuum unit 310 and an auxiliary exhaust unit 320. The embedded control unit comprises a processor 330, a memory (volatile or non-volatile), a communication bus, and an input/output unit (not shown). According to the embodiment shown in FIG. 3, the sense and control unit 250 is connected to a database 390 that can be integrated with the embedded control unit 300 or external thereto.

As shown in FIGS. 2 and 3, each of the plurality of support layer sensors 238 are connected to a respective group of the support layer inflatable members 234. Each of the support layer sensors 238 is configured to provide real time measurements relating to the pressure of a respective support layer inflatable member 234 or a respective group of support layer inflatable members 234.

Moreover, as shown in FIG. 2, a first force dispersing cover 235 may be disposed between the support layer inflatable members 234 and the coils of the layer of upper coils 231. Likewise, a second force dispersing cover 236 may be disposed between the support layer inflatable members 234 and the layer of lower coils 232.

As shown in FIG. 2, an upper buildup layer 290 is disposed above the layer of upper coils 231. The upper buildup layer 290 comprises a plurality of comfort layer inflatable members 224 that are disposed above the layer of upper coils 231 and below a topmost layer 295. The comfort layer inflatable members 224 are respectively referenced as C1, C2, C3, C4, C5, C6, C7, C8, C9, C10, C11, C12, C13, C14 and C15. The configuration of each of the respective comfort layer inflatable members 224 is similar to the configuration of the support layer inflatable members 234, discussed above.

Consistent with the embodiment depicted in FIG. 2, the comfort layer inflatable members 224 are configured such that, when inflated, the comfort layer inflatable members 224 apply forces to the layer of upper coils 231, to the upper buildup layer 290 and to the topmost layer 295. By controlling the inflation/deflation of the comfort layer inflatable members 224, the comfort characteristics of the variable sleep system 201 (among other things) can be adjusted.

Additionally, as shown in FIGS. 2 and 3, each of a plurality of comfort layer sensors 228 are connected to a respective one of the comfort layer inflatable members 224. Each of the comfort layer sensors 228 is configured to provide real time measurements relating to the pressure of a respective comfort layer inflatable member 224.

Figure 4:
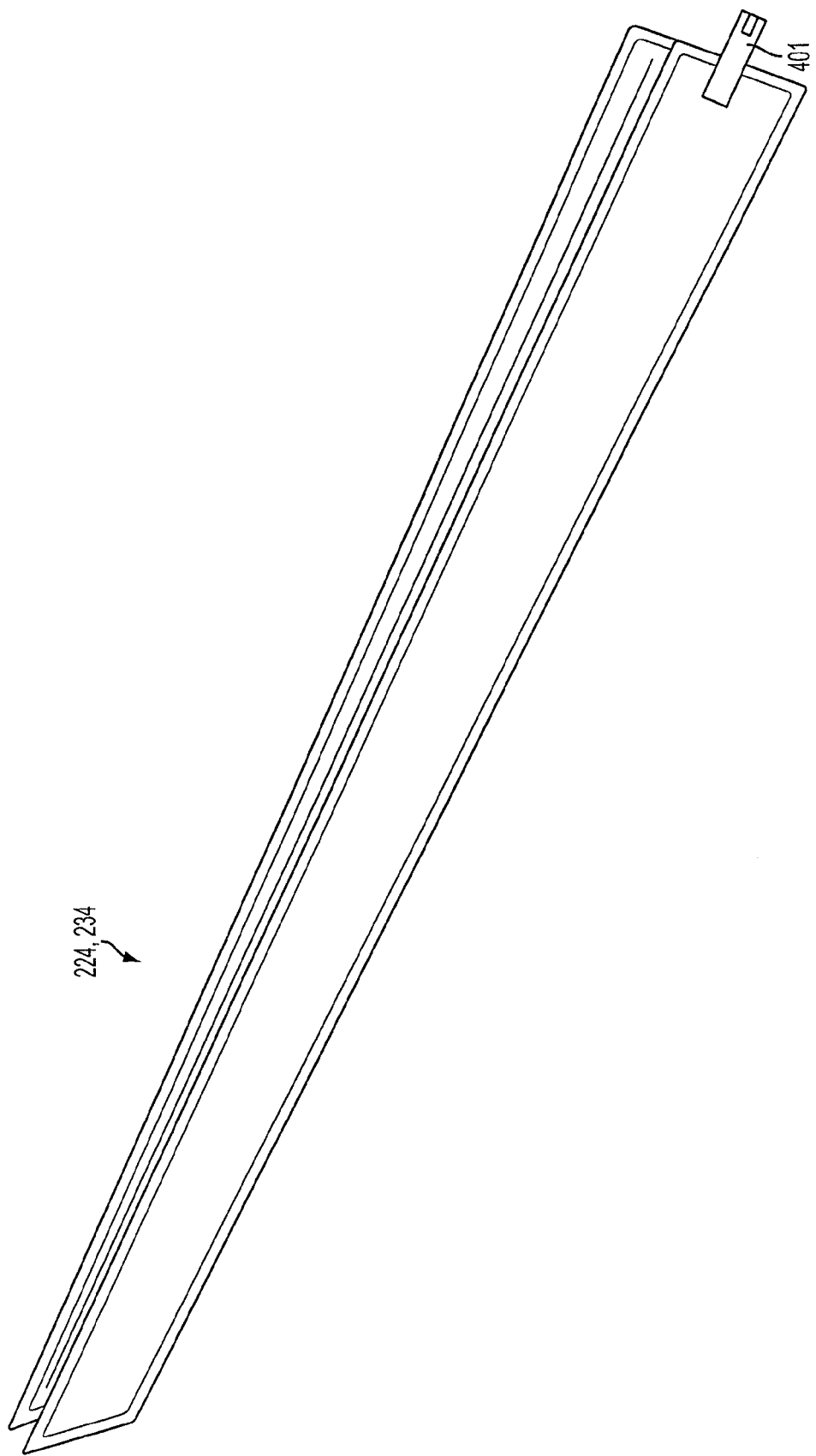
FIG. 4 illustrates a view of an inflatable member according to an illustrative embodiment of the present invention.

FIG. 4 illustrates a view of an inflatable member 224 or 234 according to an embodiment of the present invention. Although one illustrative shape and configuration of the inflatable member is shown in FIG. 4, the inflatable members 224 and 234 may assume other shapes and configurations consistent with the present invention. Further, the comfort layer inflatable members 224 may assume shapes and/or configurations that are different from the shapes and/or configurations of the support layer inflatable members 234. As shown in FIG. 4, each of the inflatable members comprises a valve 401.

Figure 7A:
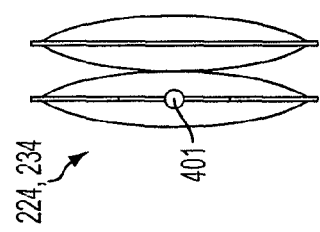
FIG. 7A illustrates a side view of one end of an inflatable member according to an illustrative embodiment of the present invention.
Figure 7B:
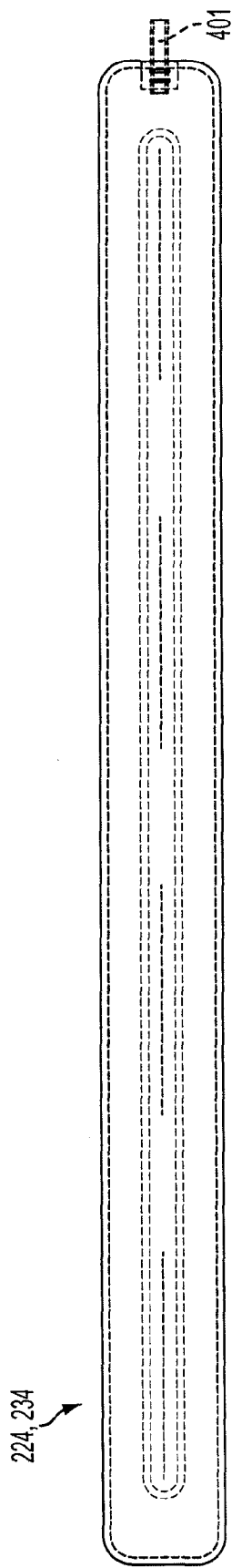
FIG. 7B illustrates a top view of an inflatable member according to an illustrative embodiment of the present invention.

FIG. 7A illustrates a side view of one end of an inflatable member 224 or 234 according to an illustrative embodiment of the present invention. FIG. 7B illustrates a top view of an inflatable member 224 or 234 according to an illustrative embodiment of the present invention.

Consistent with the present invention, the support layer sensors 238 and the comfort layer sensors 228 provide the ability to measure a wide variety of data. For example, when a person is positioned on the variable sleep system 201, data provided by the support layer sensors 238 and the comfort layer sensors 228 can be analyzed to determine, among other things, the person's weight, weight distribution, body position, body movement, breathing rate, heart rate, state of sleep, etc., Further, such data can be acquired and analyzed over time to determine a variety of body variances of the person while the person sleeps. Further, according to an embodiment of the invention, an under-mattress actigraphy device, e.g., "The Bed Sensor" from Tactex, may be employed to measure such data in addition to or in place of the support layer sensors 238 and the comfort layer sensors 228.

Accordingly, the sense and control unit 250 can automatically adjust both the comfort layer inflatable members 224 and the support layer inflatable members 234 in immediate response to body variances of the person so as to continuously provide optimal support and comfort characteristics to the person throughout the night. The data collected by the sense and control unit 250 can also be provided to the central controller 110 and analyzed together with other data collected by the central controller 110, as discussed in greater detail below.

According to the embodiment shown in FIG. 1, the sleep system 201 comprises an automatic pillow adjustment system like that disclosed by the inventors of the present application in a related provisional application U.S. Provisional No. 61/028,572 entitled "Automatic Pillow Adjustment System," which is incorporated herein by reference in its entirety. However, the present invention does not require use of such an automatic pillow adjustment system and embodiments of the present invention employ conventional adjustable and non-adjustable pillow systems.

Figure 5:
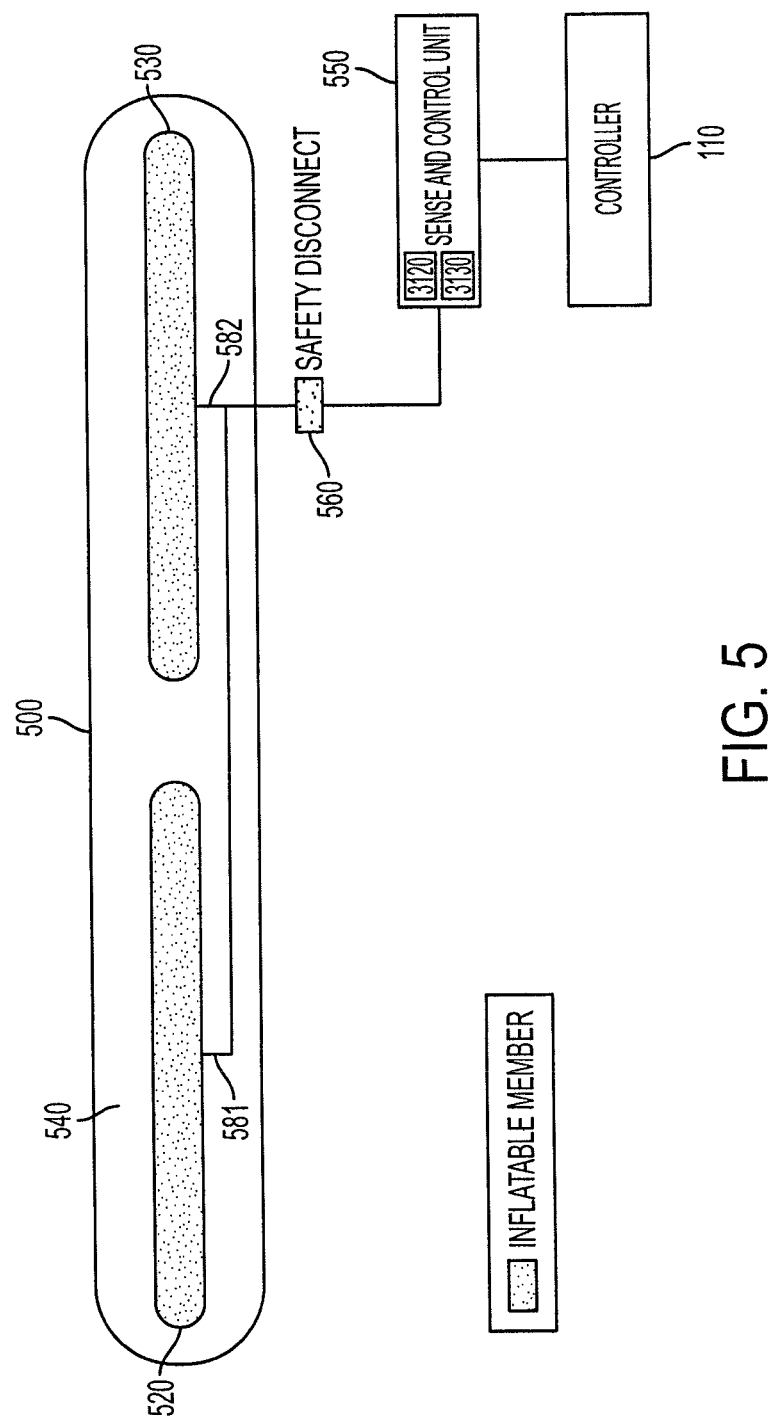
FIG. 5 illustrates a schematic cross-sectional view of an automatic pillow adjustment system according to an illustrative embodiment of the present invention.

FIG. 5 illustrates a schematic cross-sectional view of an automatic pillow adjustment system according to an embodiment of the present invention. As shown in FIG. 5, an adjustable head support member 500 comprises a first inflatable member or bladder 520 and a second inflatable member 530, which are both surrounded by an encasement layer 540. According to an embodiment, the configurations of the inflatable members 520 and 530 are similar to the configurations of the support layer inflatable members 234 and comfort layer inflatable members 224, discussed above, each with a length, width and depth suitable for use in a pillow.

As shown in FIG. 5, a sense and control unit 550 is disposed external to the adjustable head support member 500 and the inflatable members 520 and 530 are connected to the sense and control unit 550 by pneumatic tubes 581 and 582. As shown in FIG. 5, a safety disconnect unit 560 may be disposed between the inflatable members 520 and 530 and the sense and control unit 550. The safety disconnect unit 560 is configured such that, in case of entanglement, the safety disconnect unit 560 will allow the adjustable head support member 500 to come free from the sense and control unit 550. As shown in FIG. 5, the sense and control unit 550, in turn, is connected to the controller 110.

According to the embodiment shown in FIG. 5, the inflatable members 520 and 530 extend in a lateral direction across the width of the adjustable head support member 500. Further, as shown in FIG. 5, the inflatable members 520 and 530 are configured such that, when inflated, the inflatable members 520 and 530 expand and thereby apply forces to the encasement layer 540, which (among other things) supports the weight of the head and neck region of a person's body. Accordingly, by controlling the inflation/deflation of the inflatable members 520 and 530, the support characteristics of the adjustable head support member 500 can be adjusted.

As shown in FIG. 5, the illustrative sense and control unit 550 comprises a first sensor 3120, which is associated with inflatable member 520, and a second sensor 3130, which is associated with inflatable member 530. According to the embodiment shown in FIG. 5, the sensor 3120 provides real time measurements relating to the pressure of inflatable member 520 and, likewise, the sensor 3130 provides real time measurements relating to the pressure of inflatable member 530. As such, when a person positions their head on the adjustable head support member 500, measurements relating to the pressure of respective inflatable members 520 and 530 can be acquired and analyzed. Using such measurements, a support pressure profile of the person can be obtained and used to determine the most suitable pillow support characteristics for the person.

Consistent with the present invention, the sensors 3120 and 3130, together with the inflatable members 520 and 530, provide the ability to measure a wide variety of data. For example, when a person is positioned with their head on the adjustable head support member 500, data provided by the sensors 3120 and 3130 can be analyzed to determine, among other things, the sleeping position of the user. Accordingly, by analyzing the data collected by the sensors 3120 and 3130 over time, the sleeping position of the person can be determined and the pressures of the inflatable members 520 and 530 can be controlled so that the adjustable head support member 500 provides the optimal support characteristics for the person. The data collected by the sense and control unit 550 can also be provided to the central controller 110 and analyzed together with other data collected by the central controller 110, as discussed in greater detail below.

According to the embodiment shown in FIG. 1, the controller 110 is connected to an environmental data collection device 112. The environmental data collection device 112 collects data regarding environmental aspects of the bedroom 15 and the sleep system 201 and then provides this collected data to the controller 110. For example, the environmental data collection device 112 collects data regarding any of the following (or any combination or sub-combination thereof): ambient temperature, relative humidity, ambient lighting, light originating from outside the bedroom, sound levels, near-body temperature, near-body humidity, allergens, air movement, etc., However, the present invention is not limited to merely collecting the aforementioned data and embodiments of the present invention may collect any data related to the bedroom environment.

The environmental data collection device 112 may comprise, for instance, the functions of a device such as a HOBO Pendant Temperature/Light Data Logger©, or a HOBO U12 Temperature/Relative Humidity/Light/External Data Logger©, both of which are manufactured by Onset Computer Corporation. The aforementioned HOBO Data Loggers are devices that collect temperature/light intensity, or temperature/light intensity/relative humidity, respectively, and log such collected data. The environmental data collection device 112 may also comprise, for example, the functions of a sound level meter and logger, such as the Extech Sound Level Meter/Logger©, which can measure bedroom sound levels in a 30 dB to 130 dB range and log this measured data for later reference and analysis. However, the environmental data collection device 112 is not limited to the above-mentioned illustrative devices and the environmental data collection device 112 may comprise a wide variety of environmental data collection devices consistent with the present invention.

Additionally, as shown in FIG. 1, an embodiment of the present invention may comprise a near-body sensing device 117 that, for example, may be worn on the wrist of a person positioned on the sleep system 201. However, the present invention is not limited to a configuration wherein the near-body sensing device 117 is worn on a person's wrist, and embodiments of the present invention may comprise near-body sensing device(s) 117 that is/are worn on any part of a person's body, or multiple parts of a person's body. Embodiments may also comprise near-body sensing device(s) 117 that is/are integrated into aspect(s) of the bedding assembly including, but not limited to, a mattress, a bed frame, a pillow, a mattress pad, and/or linens of the sleep system 201. Alternatively, the near-body sensing device(s) 117 can be integrated into clothes in which the person sleeps, such as in pajamas. The near-body sensing device 117 may be configured to transmit data to the controller 110 via a wide variety of wired and/or wireless connections.

As a non-limiting example, the near-body sensing device 117 may comprise an Actiwatch® manufactured by Mini Mitter, which is an actigraphy device that is the size of a standard wrist watch. An Actiwatch® is equipped with a highly sensitive accelerometer, which records movement data that can be used to measure and analyze sleep quality of a person wearing the Actiwatch®.

However, such an actigraphy device is not required by the present invention. For example, according to one embodiment, as shown in FIG. 1, the sleep system 201 comprises a variable sleep system like that described in U.S. Provisional No. 61/028,591. Accordingly, as shown in FIGS. 1 and 2, the support layer sensors 238 and the comfort layer sensors 228 are employed to measure and analyze a wide variety of data including, but not limited to, the body position, body movement, breathing rate, heart rate, state of sleep, etc., of a person positioned on the variable sleep system 201. Accordingly, data collected by the sleep system 201 is used to measure and analyze the sleep quality of a person. Importantly, the present invention is not limited to the aforementioned embodiments and the sleep quality of a person sleeping on the sleep system 201 can be determined in a wide variety of ways.

According to an embodiment, the near-body sensing device 117 may comprise a near-body temperature measurement device, which is configured to measure the temperature at or near the skin of the person wearing the near-body sensing device 117.

According to another embodiment, a separate skin temperature patch, such as that used by the VitalSense® Integrated Physiological Monitoring System, which is manufactured by Mini Mitter®, can be employed to measure the temperature at or near the skin of the person disposed on the sleep system 201. However, the present invention is not limited to the aforementioned embodiments and the temperature at or near the skin of the person disposed on the sleep system 201 can be determined in a wide variety of ways consistent with the present invention. Studies have shown that the ability of a person to thermoregulate their body temperature during sleep decreases. Thus, an embodiment of the present invention uses data provided by the near-body sensing device 117 to monitor the body temperature of the person disposed on the sleep system 201 and control adjustments to the bedroom environment to help the person maintain a constant body temperature.

According to an embodiment, the near-body sensing device 117 may comprise a near-body humidity measurement device, which measures the near-body humidity of the person and transmits this measured data to the controller 110. Near-body humidity can be measured in a variety of ways and the present invention is not limited to any specific configuration of near-body humidity measurement devices. The near-body sensing device 117 may also be configured to measure skin temperature, near-body temperature, galvanic skin response, body movement (all of which can be indicative of sleep quality).

In another embodiment, the core body temperature of the person disposed on the sleep system 201 can be monitored in a variety of different ways. For example, core body temperature can be wirelessly monitored using a Jonah® Ingestible Capsule that is manufactured by Mini Mitter®. The ingestible capsule transmits a wireless signal that contains core body temperature data that can be received and recorded by the controller 110.

According to an embodiment of the present invention, the controller 110 collects and analyzes data provided by at least one of the environmental data collection device 112, and/or the near-body sensing device 117, and/or the sleep system 201 and/or the adjustable head support member 500. For example, the controller 110 collects and analyzes data from the environmental data collection device 112 including, but not limited to, at least one of data regarding the ambient temperature, and/or light intensity, and/or relative humidity, and/or sound levels, etc., in the bedroom 15. Moreover, the controller 110 may collect and analyze data provided by the near-body sensing device 117 including, but not limited to, at least one of data regarding body movement, and/or heart rate, and/or state of sleep, and/or near-body temperature, and/or near-body humidity, etc., of a person disposed on the sleep system 201. The controller 110 may also collect and analyze data provided by the variable sleep system 201, using the support layer sensors 238 and the comfort layer sensors 228 as described in U.S. Provisional No. 61/028,591, including, but not limited to, at least one of body position, and/or body movement, and/or breathing rate, and/or heart rate, and/or state of sleep, etc., of a person positioned on the variable sleep system 201. Finally, the controller 110 may collect and analyze data provided by the adjustable head support member 500, as described in U.S. Provisional No. 61/028,572, including, but not limited to, the sleeping position of the user. Such data collected by the controller 110 can be logged over the course a given night, several nights, weeks, or even months for a variety of applications, and can be analyzed using a variety of different analytical algorithms, a few examples of which are discussed below.

According to an embodiment of the present invention, after collecting data, as described above, the controller 110 then uses various analytical algorithms to determine the state of the person's sleep, such as whether the person is in a lighter stage of sleep (e.g., Stage N1) or in a deep sleep state (e.g., Stage N4). See e.g., Iber C et al., *The AASM Manual for the Scoring of Sleep and Associated Events: Rules, Terminology and Technical Specification*, 1$^{st}$ ex.: Westchester, Ill.: American Academy of Sleep Medicine, 2007. According to one embodiment, an analysis unit uses such algorithms, along with data provided by the environmental data collection device 112, to correlate changes in the person's state of sleep with changes in the bedroom environment. Any such correlations can then be provided to the person so that the person can achieve a better understanding of how the bedroom environment effects the person's sleep and so that the person can improve their overall quality of sleep by adjusting environmental variables.

For example, according to one embodiment, sleep data may be provided to the person by displaying the sleep data on a display, or by printing the sleep data on a printable medium. Further, such sleep data may be provided to a remote location using the internet or over a wired/wireless network. Sleep data may also be stored on a computer readable medium (e.g., a flash memory device or storage disk) and then provided to the person.

These algorithms can also be employed to adjust any of the following (or any combination thereof): the HVAC system 120, the lighting system 130, the ceiling fan 140, the humidifier/dehumidifier unit 155, the sound conditioner 114, the sleep system temperature adjustment unit 203 and/or the sleep system humidity adjustment unit 204. Such adjustments can be made to (among other things) promote a healthy sleep period of the person disposed on the sleep system 201 based on the state of sleep. The present invention is not limited to adjusting only the aforementioned illustrative devices, however, and the controller 110 can adjust any bedroom device consistent with the present invention.

By way of illustration of the various adjustments that can be performed, according to an embodiment, the controller 110 collects data regarding a person's sleep state from the near-body sensing device 117 and/or the variable sleep system 201. The controller also collects data regarding the ambient temperature from the environmental data collection device 112. By applying various algorithms to such collected data, the controller 110 could then determine, for instance, that the person has recently entered a lower quality state of sleep and, further, that this lower quality state of sleep corresponds to a recent increase in ambient temperature, for example, causing the person to overheat and begin to wake. Accordingly, the controller 110 would then automatically control the HVAC system 120 to decrease the ambient temperature. This would cool the person thereby promoting a higher quality sleep state for the person.

Figure 6:
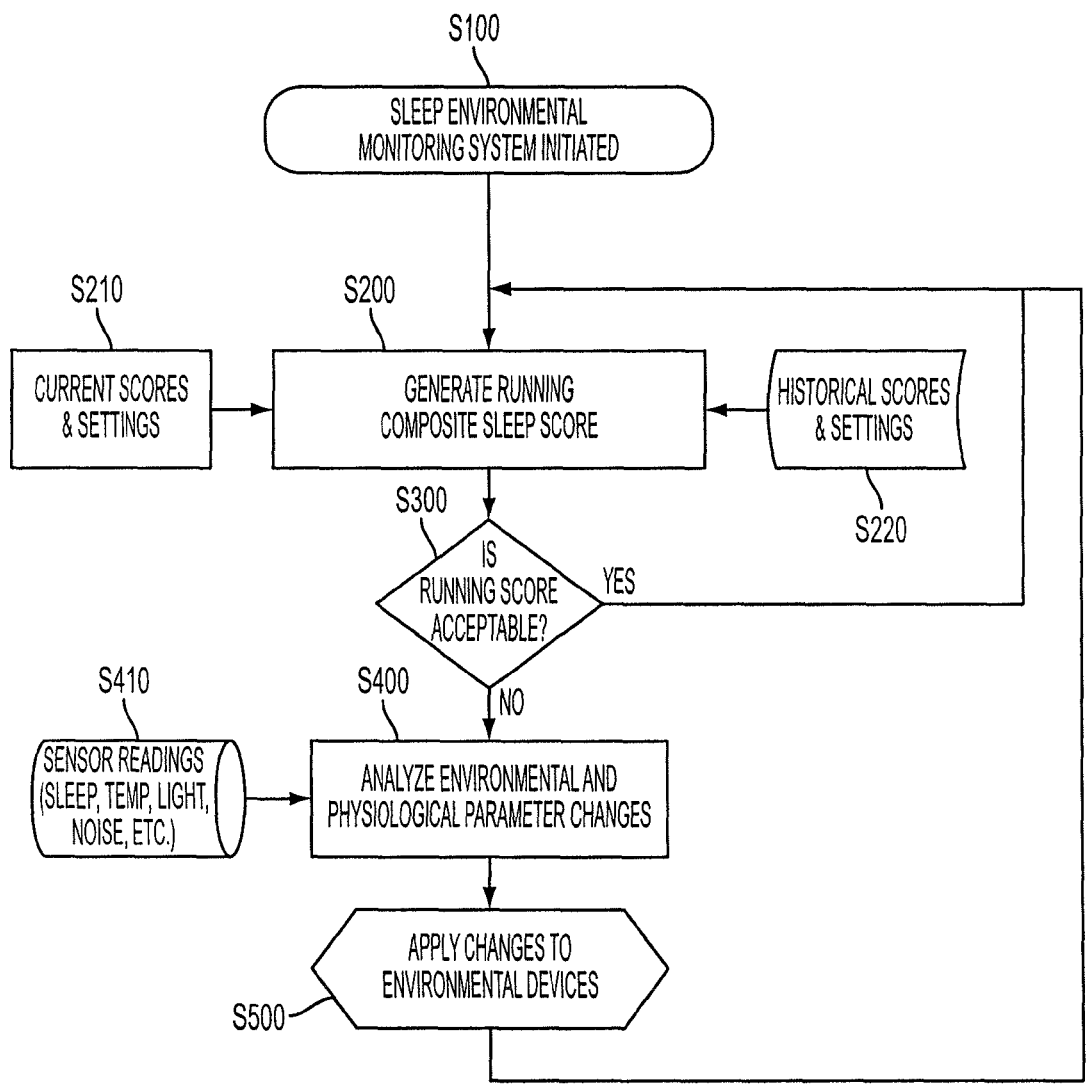
FIG. 6 illustrates a method for controlling a bedroom environment according to an illustrative embodiment of the present invention.

FIG. 6 illustrates a method for controlling a bedroom environment according to an embodiment of the present invention. As shown in FIG. 6, a sleep environmental monitoring system is initiated in operation S100. Then, in operation 5200, a running composite sleep score is generated using current sleep scores and settings generated in operation S210 and using historical scores and settings generated in operation S220. An example of a running composite sleep score is a statistical measurement that represents the person's overall quality of sleep. The composite sleep score can be generated in a wide variety of ways using a wide variety of factors, variables, algorithms and analytical techniques. As one non-limiting example, the running composite sleep score can be generated as described in U.S. Provisional Application No. 61/028,564, which is incorporated by reference herein in its entirety. In another embodiment, the composite sleep score can be based on the type and amount of movement a person makes while sleeping.

According to another embodiment, a composite sleep score can be generated using data collected regarding a person's sleep state from the near-body sensing device 117 and/or the variable sleep system 201. As environmental sleep disturbances due to environmental factors including, but not limited to, ambient noise, ambient light, etc., disturb a person's sleep state, the person's running composite sleep score will correspondingly decrease. That is, a lower running composite sleep score reflects a decrease in overall sleep quality. On the other hand, when disturbances due to such environmental factors subside, a person's running composite sleep score are likely to increase. Hence, a higher running composite sleep score reflects an increase in overall sleep quality. As shown in FIG. 6, the person's running composite sleep score is generated using current scores and settings (reflecting current measurements regarding the person's sleep state) and, if available, historical curves and settings (reflecting historical measurements regarding the person's sleep state).

In operation 5300, a determination is made as to whether the running composite sleep score is acceptable. If the running composite sleep score represents an acceptable quality of sleep for the person, then operation 5200 is performed, wherein the running composite sleep score is again generated using current sleep scores and settings generated in operation 5210 and using historical scores and settings generated in operation 5220. Whether the running composite sleep score is acceptable can be determined, for example, by comparing the running composite sleep score to a historical composite sleep score for that person. If the running composite sleep score varies significantly form the historical composite sleep score, the running composite sleep score can be deemed to be not acceptable.

If the running composite sleep score is not acceptable, suggesting that the person's overall quality of sleep is not acceptable, then operation S400 is performed wherein environmental and physiological parameter changes are analyzed using sensor readings generated in operation 5410. For instance, in operation 5410, sensor readings that are generated from the environmental data collection device 112 and the near-body sensing device 117 are analyzed to determine if there is a disturbance in the environment that may have caused the person's quality of sleep to degrade. This determination can be made, for example, by comparing the environmental sensor readings with either a threshold value, or alternatively with historical norms for the sensor readings. If one or more of the sensor readings deviates by a significant amount, then the sensor readings are analyzed to determine a possible cause of the environmental disturbance. A suitable action to counter the cause of the disturbance can then be determined. Then, in operation 5500, based on the suitable action that is determined, changes are applied to environmental devices such as the HVAC system 120, the lighting system 130, the ceiling fan 140, the humidifier/dehumidifier unit 155 and the sound conditioner 114 to promote a higher quality sleep state of the person. After operation 5500, a running composite sleep score is again generated for the person in operation 5200.

To further illustrate how the illustrative method depicted in FIG. 6 can be employed to control a person's bedroom environment to promote a higher quality sleep state of the person, according to one illustrative scenario, after the sleep environmental monitoring system has been initiated in operation S100, the person's sleep is disturbed by an increase in ambient noise (caused, for example, by noise coming from a neighboring apartment). Once the person's sleep is disturbed, the person exhibits a decrease in overall sleep quality and such a decrease is reflected by data collected regarding the person's sleep state from the near-body sensing device 117 and/or the variable sleep system 201. Further, such a decrease in overall sleep quality results in a correspondingly lower current composite sleep score being generated in operation S210. Consequently, the running composite sleep score generated in operation S200 is also lowered.

If the running composite sleep score generated in operation 5200 drops below a certain threshold and is no longer acceptable (i.e., the person's sleep is disturbed by an unacceptable amount), then operation S400 is performed wherein environmental and physiological parameter changes are analyzed using sensor readings generated in operation S410. In the above-described example regarding loud neighbors disturbing the person's sleep, the environmental data collection device 112 would detect loud ambient sound levels. Thus, in analyzing the sensor readings in operation S400, a correspondence between the loud ambient sound levels detected by the environmental data collection device 112 and the unacceptable running composite sleep score would be established. Accordingly, in operation S500, changes are applied to environmental devices (e.g., the sound conditioner 114 may be controlled, for instance, to gradually generate white noise so as compensate for the loud ambient sound levels) to promote a higher quality sleep state of the person, to generate calming nature sounds, or to generate a user's music selection. According to one embodiment, the sound conditioner 114 may be controlled to generate binaural beats so as to facilitate relaxation, improve sleep quality, decrease sleep requirements, or promote lucid dreaming.

According to another embodiment, the controller 110 collects data regarding a person's sleep state from the near-body sensing device 117 and/or the variable sleep system 201. The controller 110 also collects data regarding the ambient temperature from the environmental data collection device 112. The aforementioned data is collected over an extended period, such as several days, weeks or months. By applying various algorithms to such data collected over an extended period, the controller 110 could then determine, for instance, that a person generally experiences the highest quality sleep state when the ambient temperature is at a particular temperature that is ideal for that person. Accordingly, the controller 110 could then provide this determination to the person and/or could automatically control the HVAC system 120 to adjust the ambient temperature of the bedroom 15 to this ideal temperature when the variable sleep system 201 provides the controller 110 with data indicating that a person has positioned themselves on the variable sleep system 201. Alternatively, embodiments of the present invention could comprise a controller 110 that is configured to adjust the ambient temperature of the bedroom 15 to the ideal temperature recommended by the Better Sleep Council, which is around 65° F.

In another embodiment, the controller 110 collects data regarding a person's sleep state from the near-body sensing device 117 and/or the variable sleep system 201. The controller 110 also collects data regarding near-body temperature from the near-body sensing device 117. Some scientific studies have suggested that subtle feedback control of in-bed temperatures through very mild manipulations could enhance sleep and shift sleep to deeper stages (see e.g., "Skin Deep: Enhanced Sleep Depth by Cutaneous Temperature Manipulation," by Raymann et al., Brain: A Journal of Neurology, Volume 131, pp. 500-513, Oxford University Press, 2008, which is hereby incorporated by reference in its entirety). Embodiments of the present invention may be employed to provide feedback control of near-body temperature by, for instance, analyzing the data collected by the controller 110 regarding near-body temperature and then using the controller 110 to control the sleep system temperature adjustment unit 203 to adjust the temperature of the sleep system 201 so as to control the near-body temperature as needed to enhance sleep.

According to another embodiment, the controller 110 collects data regarding a person's sleep state from the near-body sensing device 117 and/or the variable sleep system 201. The controller 110 also collects data regarding the sound levels in the bedroom 15 from the environmental data collection device 112. By applying various algorithms to this collected data, the controller 110 could then determine, for instance, that the person has recently entered a lower quality state of sleep and, further, that this lower quality sleep state corresponds to a recent increase in sound levels (e.g., due to the noisy neighbor). In response to such collected data, the controller 110 would then automatically control the sound conditioner 114 to gradually generate white noise to drown out the recent increase in sound levels, as discussed above with respect to FIG. 6, and, thereby, promote a higher quality sleep state of the person. According to another embodiment, instead of or in addition to generating white noise, the sound conditioner 114 could generate binaural beats, generate nature sounds, or generate a user's music selection so as to promote a better sleep period for the person.

Consistent with another embodiment, the controller 110 collects data regarding a person's sleep state from the near-body sensing device 117 and/or the variable sleep system 201 over an extended period. The controller 110 also collects data regarding the sound levels in the bedroom 15 from the environmental data collection device 112 over an extended period. By applying various algorithms to such data collected over an extended period, the controller 110 could then determine, for instance, that a person generally experiences a decline in sleep quality around a specific time each night and, further, that this periodic decline in sleep quality corresponds to a periodic increase in bedroom sound levels (e.g., due to a regularly passing train). As such, the controller 110 would then provide such determinations to the person and/or automatically control the sound conditioner 114 to generate white noise shortly before the specific time of the predictable increased sound levels each night, and to stop generating white noise shortly after the increased sound levels terminate, so as to promote a better sleep period for the person. According to another embodiment, instead of or in addition to generating white noise, the sound conditioner 114 could generate binaural beats, generate nature sounds, or generate a user's music selection so as to promote a better sleep period for the person.

According to another embodiment, the controller 110 collects data regarding a person's sleep state from the near-body sensing device 117 and/or the variable sleep system 201. The controller 110 also collects data regarding the near-body temperature of the person from the near-body sensing device 117. By applying various algorithms to such collected data, the controller 110 could then determine, for instance, that the near-body temperature of the person is higher than an ideal temperature for promoting healthy sleep. Consequently, the controller 110 would then adjust the sleep system temperature adjustment unit 203 to cool the temperature of the sleep system 201 so as to compensate for the person's high near-body temperature and thereby promote a better sleep period for the person.

Consistent with another embodiment of the present invention, the controller 110 can also control ambient lighting of the bedroom 15 in accordance with a user's preferences. For instance, if a person prefers to go to sleep with a small amount of ambient lighting in the room (e.g., the person prefers to sleep with a night light), then the controller 110 can be adjusted in accordance with this preference. For example, the person can adjust the controller 110 so that it collects data from the near-body sensing device 117 and/or the variable sleep system 201 and, by applying various algorithms to this collected data, determines when the person has positioned themselves on the variable sleep system 201 (e.g., when the person is getting in bed to go to sleep). In such a case, the controller 110 automatically controls the lighting system 130 to emit a low level of ambient light (e.g., roughly comparable to a night light).

Next, the controller 110 collects data regarding, for example, the person's body movement, heart rate, breathing, sleep state, etc., from the near-body sensing device 117 and/or the variable sleep system 201. Once the controller 110 determines, from such collected data, that the person is asleep, the controller 110 then automatically controls the lighting system 130 to emit no ambient light so as to conserve electricity and promote a better sleep period for the person. Further, the controller 110 continues to collect data from the near-body sensing device 117 and/or the variable sleep system 201 throughout the night. If the controller 110 determines that the person is awake, or about to awaken, then the controller 110 controls the lighting system 130 to emit a low level of ambient light (e.g., roughly comparable to a night light).

Accordingly, whenever the person is asleep, the controller 110 controls the lighting system 130 to emit no ambient light. On the other hand, when the person is awake, or about to awaken, the controller 110 controls the lighting system 130 to emit a low level of ambient light so that the person receives the benefits of a night light (e.g., the benefits of having a low level of ambient light when trying to fall asleep and/or when walking to the bathroom during the night), without some of the disadvantages of a night light (e.g., unnecessarily consuming electricity while the person is asleep).

Indeed, such an embodiment like that described above provides many health benefits for people who prefer to sleep with a night light. For example, studies have shown that increasing production of the hormone melatonin in a person's body can improve the person's quality of sleep. Melatonin is produced by the pineal glad, normally only when a person is in darkness.

Studies have shown that women who sleep with their bedroom lights on exhibit decreased melatonin levels and an increased risk of breast cancer. Accordingly, in view of such studies, many experts recommend sleeping with no night light at all. Therefore, embodiments of the invention would help to promote a healthy sleep period by (among other things) allowing a person to fall asleep with their preferred low level ambient lighting. Once the person falls asleep, however, embodiments of the invention would adjust the bedroom lighting system to emit no ambient light and thus, the person would thereby achieve the health benefits derived from sleeping without ambient light and the person would also achieve energy savings.

Other embodiments of the present invention help to promote a healthy sleep period by (among other things) controlling a light source which eliminates only the blue component of light, for example, like those light sources manufactured by Photonic Developments, LLC. Studies have shown that using artificial light in the evening before going to bed shuts down melatonin production. In particular, studies have shown that only the blue component of light shuts down melatonin production. Using light sources with filters that eliminate only the blue component of light before going to sleep allows melatonin to be produced naturally, while the remaining colors of light allow a person to read, watch television, navigate their way to the bathroom, etc., Accordingly, embodiments of the invention help to promote a healthy sleep period by (among other things) allowing a person to fall asleep with non-blue bedroom lighting. Once the person falls asleep, however, embodiments of the invention would adjust the non-blue bedroom lighting to emit no ambient light and thus, the person would thereby achieve the health benefits derived from non-blue lighting before going to sleep, sleeping without ambient light, and the person would also achieve energy savings.

According to embodiments of the present invention, the controller 110 can control the sound in the bedroom 15 in accordance with the person's preferences. For example, if a person prefers to go to sleep with music on, then the controller 110 can be adjusted to collect data from the near-body sensing device 117 and/or the variable sleep system 201. By applying various algorithms to this collected data, the controller 110 can determine when the person has positioned themselves on the variable sleep system 201 (e.g., when the person is getting in bed to go to sleep). In such a case, the controller 10 automatically controls the sound conditioner 114 to generate the person's preferred music selection.

Next, the controller 110 collects data regarding, for example, the person's body movement, heart rate, breathing, sleep state, etc., from the near-body sensing device 117 and/or the variable sleep system 201. Once the controller 110 determines, from such collected data, that the person is asleep, the controller 110 then automatically controls the sound conditioner 114 to gradually reduce the volume of the music generated by the sound conditioner 114 over time and ultimately turn off the sound conditioner 114 as to conserve electricity and promote a better sleep period for the person. Further, the controller 110 continues to collect data from the near-body sensing device 117 and/or the variable sleep system 201 throughout the night. If the controller 110 determines that the person is awake, or about to awaken, then the controller 110 controls the sound conditioner 114 to turn on and gradually increase the volume of the sound conditioner 114 to a desired level.

In another embodiment, the controller 110 collects data regarding a person's sleep state from the near-body sensing device 117 and/or the variable sleep system 201. The controller also collects data from the environmental data collection device 112 regarding ambient light in the bedroom. The controller 110 can then be employed to control motorized window blinds or drapes disposed on the bedroom windows (not shown) to either increase or decrease the amount of natural light allowed into the bedroom in accordance with the person's state of sleep and thereby promote a better sleep period for the person.

According to one embodiment, the controller 110 is configured to collect data from the environmental data collection device 112 regarding light in the bedroom and, further, to determine the source of the light and to adjust the determined light source. For instance, the controller 110 is configured to determine whether detected bedroom light originates from a light source within the bedroom, or originates from a source external to the bedroom, such as a light in the hall, light entering through a bedroom window from the external environment, etc. Once the source of the light in the bedroom is determined, the controller 110 can then be employed to control the determined source of light. For example, the controller 110 can be configured such that if the controller 110 determines that light in the bedroom originates from a light in the hall, then the controller 110 controls the light source in the hall to reduce the intensity of light emitted therefrom. Alternatively, if the controller 110 determines that light in the bedroom originates from sunlight entering through a bedroom window, then the controller 110 can control motorized window blinds, for example, to decrease the amount of sunlight entering the bedroom through the bedroom window.

According to another embodiment of the present invention, the controller 110 collects and analyzes data provided by at least one of the environmental data collection device 112, and/or the near-body sensing device 117, and/or the sleep system 201 and/or the adjustable head support member 500, and then stores this data in the data storage device 167. Data stored in the data storage device 167 can then be extracted and transferred to a sleep laboratory in a variety of ways including, but not limited to, transfer via wireless or wired communication, transfer via storage media, manual data input, etc., so that such collected data can be further analyzed by expert sleep technicians.

Although the embodiments described above relate generally to measurement and analysis of a single person positioned on the sleep system 201, the present invention also encompasses measurement and analysis of multiple persons positioned on the sleep system 201. For example, according to an illustrative embodiment, the variable sleep system 201 may comprise two separate variable surfaces, as described in U.S. Provisional No. 61/028,591, so that the controller 110 can collect data relating to a person and their sleeping partner. Further, consistent with the present invention, multiple sensing devices 117 can be employed to collect data from different persons, respectively, and the environmental aspects of the sleep system 201 can be adjusted accordingly.

Although only a few illustrative analysis and adjustment scenarios have been described above, a person of ordinary skill in the art would readily appreciate that a wide variety of analyses and adjustments can be carried out without departing from the scope of the present invention.

The methods of controlling a bedroom environment according to embodiments of the present invention can also be embodied as computer readable codes on a computer readable recording medium. The computer readable recording medium can be any data storage device that can store data which can be read by a computer or a computer system. Examples of the computer readable recording medium include, but are not limited to, read-only memory (ROM), random-access memory (RAM), CD-ROMs, magnetic tapes, floppy disks, and optical data storage devices. The computer readable recording medium can also be distributed over network coupled computer systems so that the computer readable code is stored and executed in a distributed fashion.

While the present invention has been particularly shown and described with reference to embodiments thereof, it will be understood by those of ordinary skill in the art that various changes in form and details may be made therein without departing from the spirit and scope of the invention as defined by the appended claims. The embodiments should be considered in a descriptive sense only and not for purposes of limitation. Therefore, the scope of the invention is defined not by the detailed description of the invention but by the appended claims, and all differences within the scope will be construed as being included in the present invention.

What is claimed is:

1. A system for controlling a bedroom environment, the system comprising:
   an environmental data collector configured to collect environmental data relating to the bedroom environment;
   a sleep data collector configured to collect sleep data relating to a person's state of sleep;
   an analysis unit configured to analyze the collected environmental data and the collected sleep data and to automatically determine an adjustment of the bedroom environment, including an adjustment to a firmness of a mattress on which the person sleeps, that promotes sleep of the person; and
   a controller configured to effect the automatically determined adjustment of the bedroom environment.

2. The system according to claim 1, wherein the controller is configured to control at least one of a cooling system and a heating system.

3. The system according to claim 1, wherein the controller is configured to control a humidity adjustment unit.

4. The system according to claim 1, wherein the controller is configured to control an audio system.

5. The system according to claim 1, wherein the controller is configured to control a bedding support member temperature adjustment unit.

6. The system according to claim 1, wherein the controller is configured to control a bedding support member humidity adjustment unit.

7. The system according to claim 1, wherein the controller is configured to control a lighting unit.

8. The system according to claim 1, wherein the sleep data collector is configured to collect sleep data from a sensor positioned in or on a mattress.

9. The system according to claim 1, wherein the sleep data collector is configured to collect sleep data from a sensor positioned in or on a head support member.

10. The system according to claim 1, wherein the sleep data comprises data relating to at least one of the person's weight, the person's weight distribution, the person's body position, the person's body movement, the person's breathing rate, the person's heart rate, the person's body temperature and a near body humidity of the person.

11. The system according to claim 1, wherein the environmental data of the bedroom comprises at least one of a temperature of the bedroom, a relative humidity of the bedroom, a lighting intensity of the bedroom, and a sound level of the bedroom.

12. A method for controlling a bedroom environment, the method comprising:
    collecting environmental data relating to the bedroom environment;
    collecting sleep data relating to a person's state of sleep;
    analyzing, using at least one processor, the collected environmental data and the collected sleep data;
    automatically determining, using the at least one processor, an adjustment to the bedroom environment, including an adjustment to a firmness of a mattress on which the person sleeps, that promotes sleep of the person; and
    communicating, using the at least one processor, the automatically determined adjustment to a device that effects the bedroom environment.

13. The method according to claim 12, wherein the device comprises at least one of a cooling system and a heating system.

14. The method according to claim 12, wherein the device comprises a humidity adjustment unit.

15. The method according to claim 12, wherein the device comprises an audio system.

16. The method according to claim 12, wherein the device comprises a bedding support member temperature adjustment unit.

17. The method according to claim 12, wherein the device comprises a bedding support member humidity adjustment unit.

18. The method according to claim 12, wherein the device comprises a lighting unit.

19. The method according to claim 12, wherein the collecting sleep data comprises collecting data from a sensor positioned in or on a mattress.

20. The method according to claim 12, wherein the collecting sleep data comprises collecting data from a sensor positioned in or on a head support member.

21. The method according to claim 12, wherein the sleep data comprises data relating to at least one of the person's weight, the person's weight distribution, the person's body position, the person's body movement, the person's breathing rate, the person's heart rate, the person's body temperature and a near body humidity of the person.

22. The method according to claim 12, wherein the environmental data of the bedroom comprises at least one of a temperature of the bedroom, a relative humidity of the bedroom, a lighting intensity of the bedroom, and a sound level of the bedroom.

23. The method according to claim 12, further comprising generating a current sleep score, which comprises a statistical measurement that represents the person's quality of sleep.

24. The method according to claim 23, further comprising:
    generating a plurality of current sleep scores over time; and
    storing the plurality of current sleep scores as historical sleep scores.

25. The method according to claim 24, further comprising generating a running composite sleep score using a current sleep score and the historical sleep scores.

26. The method according to claim 25, further comprising:
    determining whether the generated running composite sleep score represents an acceptable quality of sleep for the person;
    if the generated running composite sleep score does not represent an acceptable quality of sleep for the person, then: analyzing changes to the collected environmental data and the collected sleep data;
    determining the adjustment to the bedroom environment using the analyzed changes; and
    communicating the automatically determined adjustment to the device that effects the bedroom environment.

27. The system according to claim 1, wherein the controller is configured to control blinds or drapes.

28. The system according to claim 1, wherein the sleep data collector is configured to collect sleep data relating to a plurality of persons' respective states of sleep; and
    wherein the analysis unit is configured to analyze the collected environmental data and the collected sleep data and to determine an adjustment to the bedroom environment that promotes sleep of each of the plurality of persons.

29. The system according to claim 1, wherein the analysis unit is configured to analyze the collected sleep data and to determine if the person is awake, and
    wherein the controller is configured to adjust a light source to increase intensity of light in the bedroom, if the analysis unit determines that the person is awake.

30. The system according to claim 29, wherein the analysis unit is configured such that, after determining that the person is awake, the analysis unit determines whether the person is no longer awake, and
    wherein the controller is configured such that, if the analysis unit determines that the person is no longer awake, then the controller adjusts the light source to decrease intensity of light in the bedroom.

31. The system according to claim 1, wherein the automatically determined adjustment comprises at least one of an adjustment to support characteristics of the mattress and an adjustment to comfort characteristics of the mattress.

32. The system according to claim 1, wherein the sleep data collector is configured to automatically collect the sleep data relating to the person's state of sleep.

33. A non-transitory computer readable storage medium comprising instructions for causing a computer to execute a method comprising:

collecting environmental data relating to the bedroom environment;

collecting sleep data relating to a person's state of sleep;

analyzing the collected environmental data and the collected sleep data;

automatically determining an adjustment to the bedroom environment, including an adjustment to a firmness of a mattress on which the person sleeps, that promotes sleep of the person; and communicating the automatically determined adjustment to a device that effects the bedroom environment.

34. The method according to claim 12, further comprising:

analyzing the collected sleep data to determine if the person is awake, and if it is determined that the person is awake, adjusting a light source to increase intensity of light in the bedroom.

35. The method according to claim 34, further comprising:

after determining that the person is awake, later determining whether the person is no longer awake, and if it is determined that the person is no longer awake, then adjusting the light source to decrease intensity of light in the bedroom.

36. The method according to claim 12, wherein the automatically determined adjustment comprises at least one of adjusting support characteristics of the mattress and adjusting comfort characteristics of the mattress.

37. The method according to claim 12, wherein the collecting sleep data comprises automatically collecting sleep data relating to the person's state of sleep.

38. The system according to claim 1, wherein the sleep data collector is configured to collect sleep data from a sensor positioned on the person.

39. The system according to claim 38, wherein the sensor positioned on the person comprises an actigraphy device.

40. The method according to claim 12, wherein the collecting sleep data relating to a person's state of sleep comprises collecting sleep data from a sensor positioned on the person.

41. The method according to claim 40, wherein the sensor positioned on the person comprises an actigraphy device.

42. A system for providing sleep data, the system comprising:

an environmental data collector configured to collect environmental data relating to a bedroom environment;

a sleep data collector configured to collect sleep data relating to the person's state of sleep;

an analysis unit configured to analyze the collected environmental data and the collected sleep data and to automatically correlate changes in the person's state of sleep with changes in the bedroom environment, including an adjustment to a firmness of a mattress on which the person sleeps, that promotes sleep of the person;

a data providing unit configured to provide data relating to said automatic correlation; and an adjustment unit configured to perform the adjustment.

43. The system according to claim 1, wherein the automatically determined adjustment comprises an adjustment to spinal alignment characteristics provided by the mattress to the person.

44. The system according to claim 1, wherein the automatically determined adjustment comprises an adjustment to interface pressure characteristics provided by the mattress to the person.

* * * * *